(12) United States Patent
Bormet (10) Patent No.: US 12,379,583 B2
(45) Date of Patent: Aug. 5, 2025

(54) ENDOSCOPE SYSTEM WITH ADAPTIVE LIGHTING CONTROL

(71) Applicant: KARL STORZ Imaging, Inc., Goleta, CA (US)

(72) Inventor: Jonathan Bormet, Goleta, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 0 days.

(21) Appl. No.: 18/391,548

(22) Filed: Dec. 20, 2023

(65) Prior Publication Data
US 2024/0264424 A1 Aug. 8, 2024

Related U.S. Application Data

(63) Continuation of application No. 17/557,434, filed on Dec. 21, 2021, now Pat. No. 11,892,617.

(51) Int. Cl.
*H04N 23/80* (2023.01)
*G02B 23/24* (2006.01)

(52) U.S. Cl.
CPC ..... *G02B 23/2484* (2013.01); *G02B 23/2469* (2013.01); *H04N 23/80* (2023.01)

(58) Field of Classification Search
CPC . G02B 23/2484; G02B 23/2469; H04N 23/80
USPC .......................................................... 348/68
See application file for complete search history.

(56) References Cited

U.S. PATENT DOCUMENTS 10,924,689 B1 * 2/2021 Duckett, III ........... H04N 23/55

FOREIGN PATENT DOCUMENTS

EP 3061385 A1 * 8/2016 ......... A61B 1/00006

* cited by examiner

*Primary Examiner* — Nguyen T Truong
(74) *Attorney, Agent, or Firm* — David N. Villalpando; Jacqueline Cohen (57) ABSTRACT

The present invention relates to a method for producing adaptive lighting controls for an endoscope with multiple light emitting elements such as distinct light fibers, or distinct distal light emitting diodes (LEDs), etc. The amount of light delivered to the scene can be locally adjusted on a per-light basis to manage the dynamic range of the scene. For example highly reflective metallic tools many benefit from reduced light, while cavities may benefit from increased light projected into the lumen.

19 Claims, 7 Drawing Sheets

ENDOSCOPE SYSTEM WITH ADAPTIVE LIGHTING CONTROL

TECHNICAL FIELD

The present invention relates to a system for an illumination system for viewing instruments, such as endoscopes. More specifically, the present invention relates to an apparatus for endoscopic adaptive lighting control as well as a corresponding method.

BACKGROUND

Many medical investigations and surgical procedures are performed by endoscopic means today. Consequently the strain on a patient can be considerably reduced. However, because of the reduced visual field as a result of endoscopic access, endoscopic procedures require considerable practice on the part of the operator to make accurate estimates of the distance to a surface of an interior body cavity in which a surgical manipulation is to be performed. These devices are often used in challenging high dynamic range (HDR) scenes which may include specular highlights from wet anatomy, deep lumens, and highly reflective metallic tools. It is difficult to properly expose such a scene because the amount of signal received by each pixel of the imager can vary significantly.

Existing HDR techniques have various shortcomings. Typically, the algorithms that combine images at different exposures require some amount of overlap in the instantaneous dynamic range of each image. Because the light intensity associated with a highlight or metallic tool may be many orders of magnitude brighter than the surrounding tissue, it may be necessary to acquire an unreasonable number of images spanning these extremes with sufficient overlap in adjacent exposures.

Figure 1A:
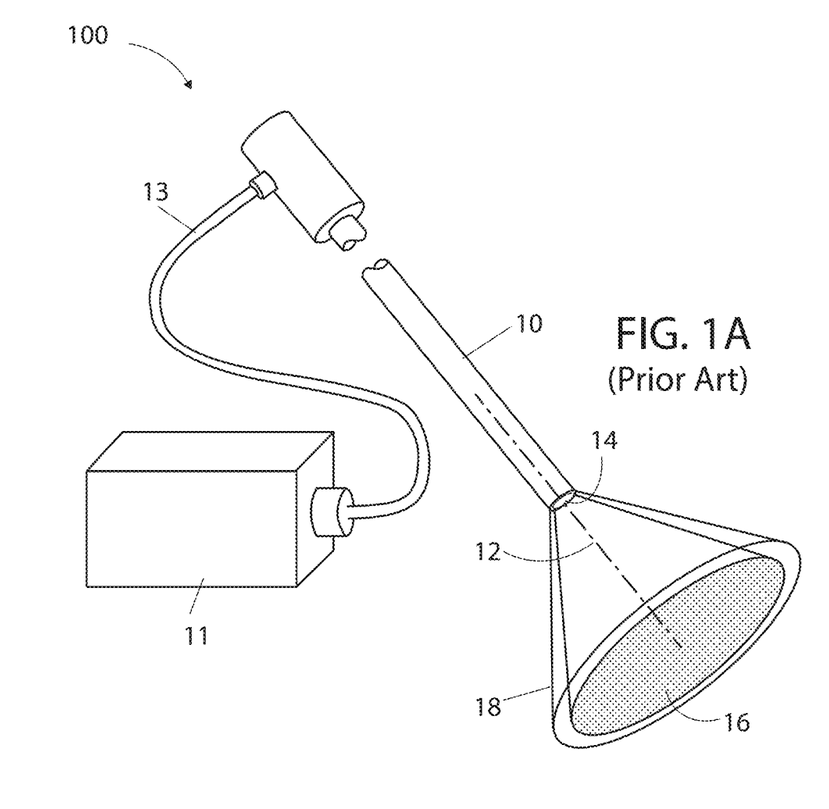
FIGS. 1A-C are schematic views of endoscopic illumination systems existing in the prior art.
Figure 1B:
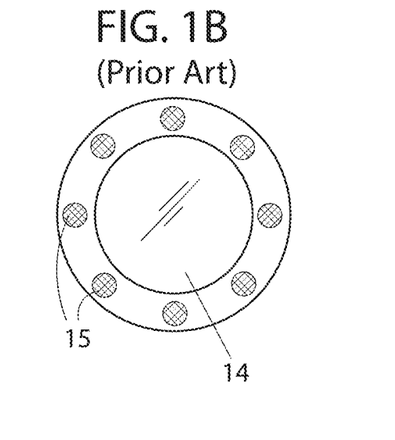
Figure 1C:
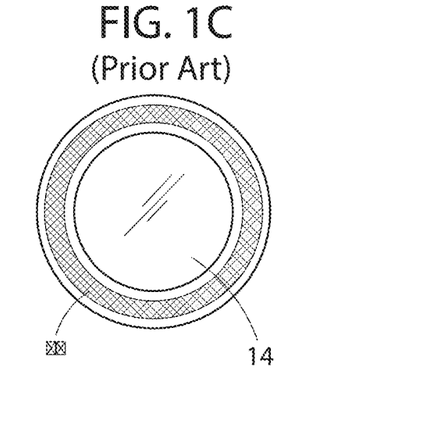

FIG. 1A illustrates a basic illumination system 100 for a traditional endoscope 10. Generally, an endoscope 10 has a fixed line of sight 12 through an objective lens 14. The endoscopic field view field 16 is covered by an illumination field 18, which is typically generated by a remote source 11 and transmitted via a fiber optic light guide 13. The illumination field 18 is designed to cover the entire view field 16 to ensure uniform image brightness. To this end, the illumination field 18 is typically designed to be radially symmetric about the objective lens 14, with light issuing from evenly distributed fiber optic outlets 15, as is shown in FIG. 1B, or a single annular outlet 17, as illustrated in FIG. 1C.

U.S. Pat. No. 7,668,450B2 entitled "ENDOSCOPE WITH INTEGRATED LIGHT SOURCE" to Todd, et al. teaches an LED based light source unit for an endoscopic imaging system that produces illumination for a camera through an endoscope. The light source unit includes an array of LEDs mounted to a thermally conductive substrate. The light source unit is integrated into the proximal end of an endoscope and coupled directly to the optical fibers running to the tip of the endoscope. A number of such light source units may be integrated into the housing of an endoscope. Light emitted from each light source unit is directed to a distinctive section of the endoscope's tip and a doctor may control light output of each individual light source unit during a surgery. However, this reference requires manual control of the light source unit and on color temperature manipulation. This manual control is undesirable as it requires a doctor to manually control the lighting during endoscopic procedures, and may be an undesired burden on doctors.

US Patent Publication No. 20090149713A1 entitled "ENDOSCOPE APPARATUS" to Niida teaches an endoscope apparatus including a CCD and a number of LEDs for illuminating the field of vision for image pickup of the CCD. In this reference, the image is partitioned into a grid, and the illuminators are structured in the same manner. A number of LEDs are arranged at positions corresponding to the areas illuminated by each of the LEDs in a straightforward manner—i.e., the top left illuminator hits the top left grid area in a one-to-one correspondence that seems to be used throughout. Niida does not contemplate or describe how the perform adaptive lighting control when illumination areas may overlap, or how to manage cases of controlling multiple illuminators that overlap, or how the details of this overlap will vary depending on scene geometry. Near vs far, or centered vs decentered objects, etc. will all tend to undermine this grid assumption.

U.S. Pat. No. 10,594,946B2 entitled "OTOSCOPE WITH CONTROLLED ILLUMINATION" to Govari et al. teaches multiplicity of illuminators arrayed around the objective lens and configured to illuminate the object, and a processor which is coupled to differentially adjust respective light intensities emitted by the illuminators responsively to the signal and that a one-to-one correspondence is not assumed, as with the previous reference. They describe calibrating the system using a planar target to obtain a matrix that maps out the way the light sources superimpose on the target. They also acknowledge that for anything other than this planar calibration target, there will be a distortion of this mapping due to the 3D structure of the scene. They essentially use the calibration result as an initial seed for an unknown target, and then differentially adjust until the illumination is re-calibrated for the current scene.

Patent application DE 10 2006 017 003 A1 teaches an endoscope for depth acquisition in which a modulated light signal is emitted and the modulation parameters of the received light signal are used to compute the depth data. Via a plane semi-transparent mirror used as a beam splitter, beams can be received by two image sensors, one of which captures the modulation parameters useful for generating 3D data while the other is provided to capture a visual image of the endoscopic scene.

In US 2006/0025692 A1, an endoscopic apparatus for generating an endoscopic fluorescence image is described, such that a distancing signal is generated by a distance-measuring unit, operating for example with ultrasound, microwaves or laser light. However, the reference does not describe how to use a common center of projection beam splitter such that light-to-region correspondence is not tentatively assumed, but is determined by the optical design for an arbitrary scene geometry.

Patent application DE 10 2008 018 636 A1, which is incorporated herein by reference in the present application in full, teaches an apparatus for endoscopic 3D data collection, which includes light-generating means for generating at least a modulated measuring radiation, light-transmitting means for transmitting the measuring radiation onto an object to be observed and light-imaging means for imaging a signal radiation from an object to be observed onto a phase-sensitive image sensor. By evaluating the data provided by the phase-sensitive image sensor, 3D data on the observed object are generated. The collection of absolute 3D data is not foreseen by this apparatus.

Publication WO 94/03100 teaches a method for depicting the interior of bodies, where a spatial data field is associated with a body situated in a particular position and the spatial position of a video camera, before which an endoscope is mounted, is recorded on a continuous basis. In addition, a depiction of a data field, which corresponds in each case to the current viewing angle of the video camera, is computed and the optical image and data field are simultaneously displayed on the monitor. By means of an input process by the user, one or more characteristic points of the data field are harmonized with the associated optical depiction on the screen. For the data field, it is possible to use a three-dimensional reconstruction, which is acquired from one or more previously shot video recordings, with which a distance measurement via ultrasound or by stereometric analysis is associated. The ultrasound distance measurement, however, allows the collection of only relatively few data points, while a stereometric analysis is restricted to high-contrast surfaces. Therefore, and because of the necessary interaction of the user, the usability of the method and the resulting advantages are restricted.

Patent DE 10 2004 08 164 B3, which is incorporated herein in the present application by reference in full, discloses an apparatus for producing at least a portion of a virtual 3D model of a bodily interior, the apparatus including an endoscope, a positioning system with an inertial sensing system to record the position and orientation of the endoscope, and a distance-measuring system to acquire at least one distance of the endoscope from at least one point on the surface of the bodily interior. Distance is measured with the help of a laser beam emitted by the endoscope on the basis of a triangulation or by run-time measurement of the laser beam or with the help of a pattern projected by the endoscope onto the surface of the bodily interior or else by ultrasound. From points on the surface of the bodily interior recorded by the distance-measuring system, a portion of a virtual model of the surface of the bodily interior is produced. Because this necessitates distance measurement from a number of different positions and orientations of the endoscope, only a relatively low spatial resolution can be achieved.

In an article by Höller et al. "Spatial Orientation in Translumenal Surgery," in Minimally Invasive Therapy 19 (2010): 282-273, a flexible endoscope is described, on whose proximal end a time-of-flight (TOF) sensor is mounted. An inertial sensor is positioned at the distal end of the endoscope in order to establish the endoscopic image on a gravitational basis or to provide a corrected image horizon. However, an inertial sensor requires a relatively large structural area, and therefore cannot easily be integrated into a distal end portion, especially in flexible endoscopes with small diameter.

SUMMARY OF THE INVENTION

Accordingly, it is an object of the present invention to provide an illumination system for a scope that provides adaptive lighting.

It is a further object of the present invention to provide an illumination system for a scope that can provide illumination using a number of lighting elements where the correspondence between lighting elements and scene regions is not assumed, but rather computed.

It is yet another object of the present invention to provide an illumination system for a scope that can provide white light (WL) and infrared (IR) illumination.

It is still another object of the present invention to provide an illumination system for a scope that automatically adjust the illumination of a captured scene without requiring manual adjustments from a user. Adaptive lighting may be performed automatically, for example, by execution of electronic-based software and/or hardware.

In order to overcome the deficiencies of the prior art and to achieve at least some of the objects and advantages listed, the present application includes an endoscope system including a number of lighting elements located at a distal end, a camerahead for capturing a first set of one or more images of a scene that is illuminated by the number of lighting elements, and software and/or hardware including at least one process, wherein the at least one process is configured to: determine correspondences for a number of regions of the scene based on the first set of one or more images, determine measured light intensities at the number of regions, determine drive strengths for the lighting elements based on the correspondences and the measured light intensities, and cause the drive strengths to be applied by the lighting elements.

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. The use of the same reference numerals indicates similar but not necessarily the same or identical components; different reference numerals may be used to identify similar components as well. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

DETAILED DESCRIPTION

Existing HDR techniques have various shortcomings. Typically the algorithms that combine images at different exposures require some amount of overlap in the instantaneous dynamic range of each image. Because the light intensity associated with a highlight or metallic tool may be many orders of magnitude brighter than surrounding tissue, it may be necessary to acquire an unreasonable number of images spanning these extremes with sufficient overlap in adjacent exposures. Adaptive lighting that reduces the extremes seen by the imager may be more effective in some cases, particularly if the dynamic range of the illumination is comparable to or much greater than the dynamic range of the imager.

In endoscopic camera systems as well as exoscopes, lighting is often provided by multiple light emitting elements such as distinct light fibers, or distinct distal LEDs etc. Through use of a dimmer mechanism (e.g., pulse width modulation of LEDs, use of a digital light processor/digital mirror device, an LCD like mechanism, etc.) the amount of light delivered to the scene can be locally adjusted on a per-light basis to manage the dynamic range of the scene. For example highly reflective metallic tools many benefit from reduced light, while cavities may benefit from increased light projected into the lumen. According to various embodiments described herein, the amount of analysis process could guide a physical re-lighting of the scene to improve illumination quality.

The present application is relevant to endoscope systems used with proximal cameraheads where light is delivered via two or more lighting elements (e.g., light fibers or LEDs), videoendoscopes using two or more distal LEDs, as well as exoscopes with two or more exit ports for illumination. The lighting elements may be independently controlled so that some may be brighter than others. Furthermore, regions of interest may be illuminated by multiple lighting elements in an overlapping manner. For example, a first lighting element and second lighting element may be projected to region such that they partially overlap, one fully overlaps the other, and so forth. In various embodiments, adaptive lighting controls described here may be used to deliver, using multiple lighting elements that may have overlapping illumination regions, different amounts of light to different regions. For example, the intensity of light.

In the prior art, image processing techniques have been used to capture an image (a "raw image") and perform digital imaging post-processing to digitally re-light a scene through manipulation of the image intensity values. In contrast, embodiments according to the present application directly modulate the light elements illuminating the scene to achieve a similar effect. This can lead to improved noise performance relative to using digital gain to manipulate an under exposed sensor region, and improved highlight behavior in regions that would ordinarily be overexposed and clipped on the imager.

The present application may be particularly useful in resectoscope applications where the surgeon desires to see both a metallic cutting tool and the background tissue, but the unwanted reflections from the extending/retracting arms cause a varying degree of interference in the image.

The devices described herein are often used in challenging high dynamic range scenes which may include a wide range of anatomy that may include both regions that are highly-reflective and others that are less reflective. For example, a typical environment may include specular highlights from wet anatomy, deep lumens, and highly reflective metallic tools. Furthermore, certain regions such as cavities may require more illumination. These highly-reflective and less reflective regions may be interspersed within a scene, making it difficult to properly illuminate a scene. Accordingly, it may be difficult to properly expose such a scene as the amount of signal received by each pixel of an image may vary significantly.

In at least one embodiment, the distal end of an endoscope tip may include at least a beam splitter/projector type system using a common center of projection such that the light-to-region correspondence is computed—rather than tentatively assumed—based on the optical design for arbitrary scene geometries.

In at least one embodiment, illumination elements are not co-sited, and stereo triangulation techniques may be used to compute the light-to-region correspondence. Real-time or near real-time stereo triangulation may be performed using structured light. In various embodiments, a beam splitter is used to project an infrared pattern (e.g., constellation) onto a scene. The infrared pattern may have a predetermined geometry, such as concentric circles, horizontal and/or vertical bars, and so forth. The projected pattern may be captured and then processed to identify any deformations based on the geometry of the scene that the pattern was projected on. Based on these deformations, a light-to-region correspondence may be computed, rather than tentatively assumed. The use of infrared or near-infrared bands may be used to avoid interfering with visible imaging. The same correspondence information can be directed used when adjusting the white light illumination spot associated with a particular NIR point. Imaging rays of the camera—which may be referred to as "correspondence rays"—associated with a stereo triangulation system may be used, and the scene illumination rays can have a more general relationship than those described so far. With this approach, triangulation may be performed once to determine the 3D scene relative to an imager, and an additional triangulation may be computed to associate illumination rays with 3D scene regions.

In at least one embodiment, intensities of a number of lighting elements (e.g., LEDs) that project onto overlapping regions are dynamically adjusted. A camerahead captures video frames that are analyzed to determine whether scene regions predominantly illuminated by a particular lighting element are over or under exposed. These region-based image metrics are in turn used to compute an appropriate adjustment to the drive level of each lighting element. Further image processing can compensate for the fact that different regions receive different amounts of light, for example, by adjusting (e.g., normalizing) the intensity of light projected on to each region. This approach has various benefits over post-processing techniques such as high dynamic range (HDR) illumination. In an HDR scene, the dynamic range of a typical imager is limited, and the illumination may exceed the range of a typical imager. In contrast, by adjusting the drive levels of the respective lighting elements rather than performing post-processing adjustments, the reflectance and illumination of a scene may be normalized so that a typical imager is able to capture the full range of tonal values within a high contrasted scene.

One aspect of the invention is the use of a number of lighting elements that whose illumination regions may overlap and change, based on the topography of the scene. How different lighting elements contribute to the illumination of a scene may be complex to compute, involving determination of various three-dimensional factors such as distance to target, scene geometry, etc., that may be difficult to ascertain from a camerahead capturing 2D images. For example, endoscopes may be used to provide video or images of a hollow organ or cavity in a body with varied topography, depth, etc. that affect how much each lighting element contributes to the illumination of a particular pixel or region. Furthermore, the contributions of each lighting element to each pixel may be expected to change as different regions are examined during an endoscopic procedure.

In at least one embodiment, images are extracted from a video feed of an endoscopic camera system. A base image is computed with estimates of local light levels in order to synthesize a new image wherein the image may be digitally re-lit through manipulation of image intensity values. Similar local intensity information may be used to directly modulate the lighting elements illuminating the scene to achieve a similar effect. This can lead to improved noise performance relative to using digital gain to manipulate an under-exposed sensor region, and improved highlight behavior in regions that would otherwise be overexposed and clipped on the imager.

Determining which lighting elements correspond to which regions of a captured image may be non-trivial as it generally depends on understanding how different elements of a 3D scene map onto a 2D image. Various factors such as distance to target, scene geometry, etc. affect how different lighting elements contribute to the illumination of a scene.

In at least embodiment, light on non-visible wavelengths may be used to project structured patterns to a scene. These structured patterns may be projected on wavelengths beyond the visible spectrum, for example, as infrared signals. A constellation pattern may be spatially encoded into an illumination using near-infrared (NIR) wavelengths ranging from 0.7 to 1.4 microns. The use of NIR or other non-visible light does not interfere with visible imaging. In some cases, visible light may be used to temporarily project structured light frames through the use of a frame buffer—for example, if a camerahead captures video at a rate of 60 frames per second, structured light may be projected for $1/60^{th}$ of a second, $2/60^{th}$ of a second, etc. In various embodiments, a structured pattern is projected on a visible wavelength by temporally sequencing between normal frames and structured light frames hidden from the user through use of a frame buffer. Even without a dense projection, such as for example only two distinct light elements illuminating the left and right half of the scene, the system could sequence between left-only, right-only, and left and right, for example, to correlate the contribution of each light element to each region within the scene.

In at least one embodiment, a camera or arrangement of multiple cameras may be used to project a pattern (or an arrangement of multiple patterns). For example, a pattern may be projected using a depth camera. An example of a depth camera is a Microsoft Kinect Sensor that emits light (e.g., infrared spectrum) and determines scene depth information using structured light. One way in which projected patterns may be used to generate a depth map by triangulating between a known ray of source light and an image ray received by the sensor. The constellation pattern facilitates establishing correspondence. According to various techniques described herein, such correspondence information between light sources and image locations may be used to control the intensity of the illumination of lighting elements to provide for better overall illumination of a scene.

While the techniques described above include visible light imaging by using a projected NIR structured light pattern, the principles of the present disclosure are not limited to visible light imaging. For example, techniques described herein can be applied to other types of imaging. The same principles could be applied in the context of indocyanine green (ICG) imaging, where the roles of visible light and NIR light are interchanged: a visible light projection would, in such embodiments, be used to project a structured light pattern using a visible light projector and a NIR light for excitation light and an NIR camera for imaging ICG emissions.

Figure 2:
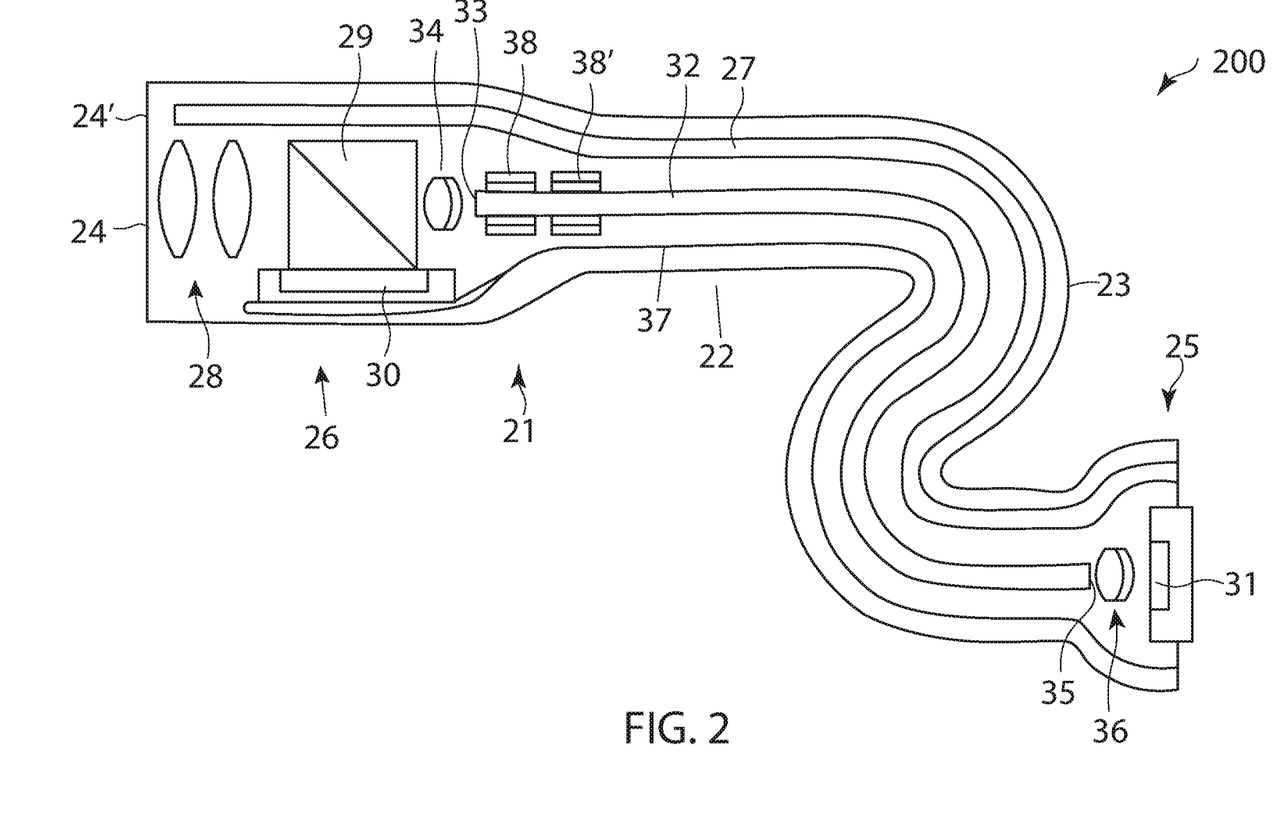
FIG. 2 is an example process flow diagram for automating endoscopic device actions in accordance with one or more embodiments of the disclosure.

As shown in FIG. 2, an endoscope 21, according to an additional embodiment of the present application, includes an elongated flexible shaft 22. The shaft 22 includes a flexible outer shaft 23, which is concluded in its distal end portion by one or more distal windows 24, 24'. Additional optical, mechanical and electronic components are enclosed inside the flexible outer shaft. Situated in the proximal end portion of the shaft is an endoscope head 25, which for example can include control elements to control the endoscope tip, that is, the distal end portion 26, as well as irrigation and suction connectors (not illustrated). In addition, a light-conducting cable to connect with a light source as well as electrical supply and signal cables can also be coupled on the endoscope head 25 (not illustrated).

Measuring radiation and illumination light are guided through a light conductor 27 to the distal end portion 26 of the endoscope 21 and, in some cases, conducted via a non-illustrated widening lens through the window 24' to a surface area of an internal bodily cavity. The light conductor 27 consists of a glass fiber bundle and is of flexible configuration.

Signal radiation enters from the observed area of the surface of the cavity through the window 24 into the endoscope objective lens 28 and is divided by the beam splitter 29 into a portion that arrives at an image sensor 30 situated in the distal end portion 26 in the longitudinal direction of the shaft 22, and another portion that is transmitted to an image sensor 31 situated in the endoscope head 25. To transmit the corresponding portion of the signal radiation to the image sensor 31, inside the shaft 22 a flexible image conductor 32 is situated consisting of an ordered bundle of optic fibers. On the distal end surface 33 of the image conductor 32, the portion of the signal radiation is imaged by an adaptive lens 34. The numerical aperture is adjusted by the adaptive lens 34 in order to allow optimal use of the optic fibers. According to a non-illustrated embodiment, the image conductor 32 can be cemented onto the proximal-end outlet surface of the beam splitter 29, wherein the cement preferably has a refractive index that is equal to that of the fiber core or between that of the fiber core and that of the beam splitter 29. From the proximal end surface 35 of the image conductor 32, an image is generated by an imaging lens 36 onto the sensor surface of the image sensor 31. An electric line 37, likewise mounted inside the shaft 22, serves to supply the distal image sensor 30 and for data transmission. Light-conducting cables and electric cables to connect the light conductor 27 or the line 37, as well as to connect the image sensor 31 with a non-illustrated control and evaluation device, can be connected to the endoscope head 25.

Coils 38, 38' of an otherwise non-illustrated position-sensing or position-recording system are situated in the distal end portion 26. The coils 38, 38' surround the image conductor 32 in its distal end portion; the coils 38, 38' in this manner can be situated inside the shaft 22, without it being substantially enlarged in diameter. At least in the area of the coils 38, 38', the outer shaft 23 as well as, in some cases, other surroundings and reinforcements are of non-metallic construction, so as not to disturb the functioning of the position-sensing system. From the coils 38, 38', non-illustrated electric lines are lead inside the shaft 21 to the endoscope head 25 and likewise cause no enlargement of the shaft diameter. Because the coils 38, 38' are situated in the distal end portion 26 of the shaft 22, the coils stand in a fixed geometric relationship to the distal end of the shaft, in particular to the endoscope objective lens 28, to the image generated by it on the distal image sensor 30, and to the image generated by the endoscope objective lens 28 via the adaptive lens 34 on the distal end surface 33 of the image conductor 32. In various embodiments, image sensor 31 measures a structured light (SL) pattern that is projected onto a scene, and thereby determines 3D data relating to the scene based on deformations of the SL pattern. For example, a predetermined pattern of a series of horizontal and vertical bars may be projected onto a scene, and 3D information may be determined based on how the bars are deformed in a captured image.

Figure 3:
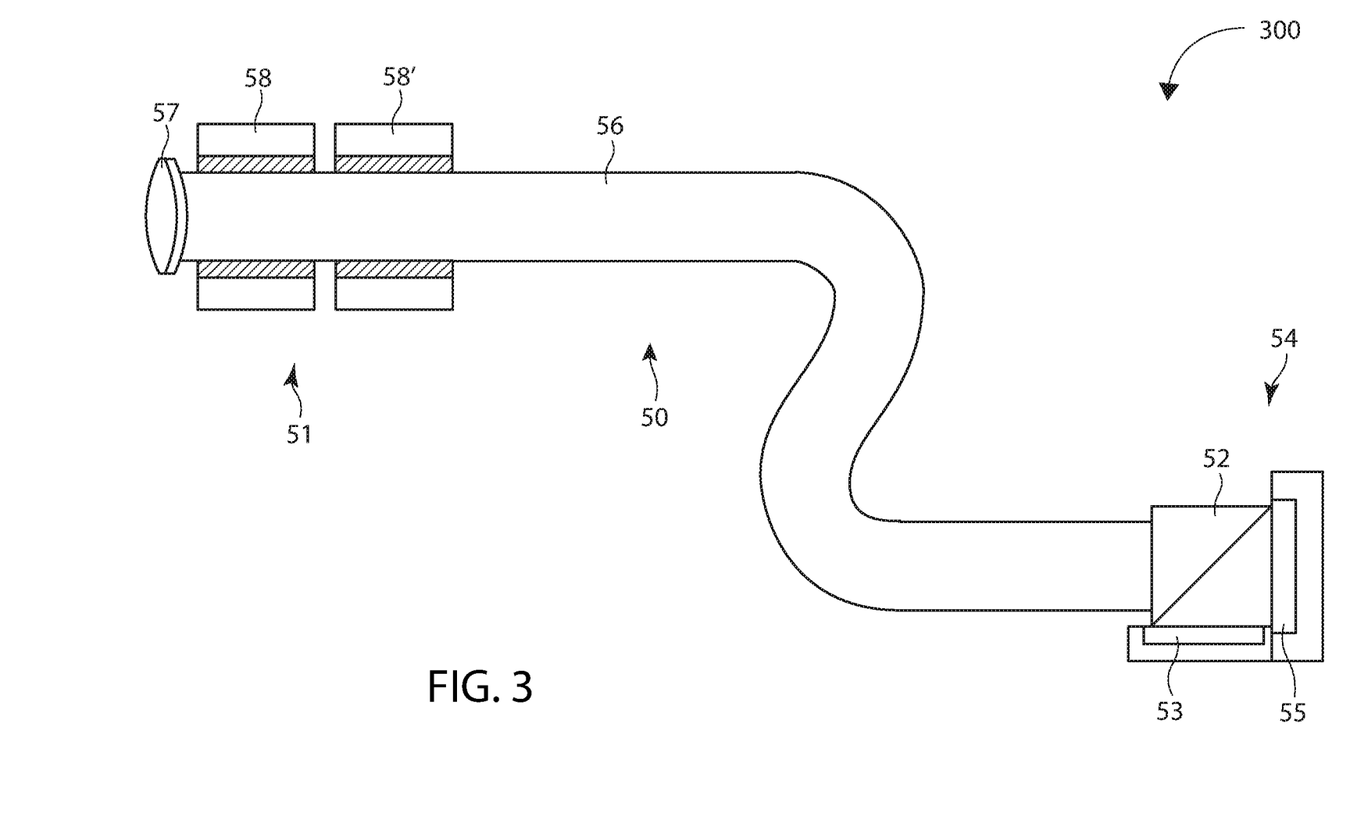
FIG. 3 depicts an example hybrid process and data flow in accordance with one or more embodiments of the disclosure.

FIG. 3 shows in simplified schematic depiction an additional embodiment of a flexible endoscope 50 as part of an inventive apparatus. The embodiment shown in FIG. 3 is distinguished from that shown in FIG. 2 in that a beam splitter 52 and an image sensor 53 are not situated in the distal end portion 51 but rather in the proximal end portion 54 of the endoscope 50. An image sensor 55 is also situated in the proximal end portion 54. The beam splitter can, for example, deflect a portion of the signal radiation to generate a visual image of an area of the internal bodily cavity onto the image sensor 53 and can pass the portion of the signal radiation used to generate the 3D data onto the image sensor 55; the arrangement of the image sensor 53 and of the image sensor 55 can also be reversed.

Inside a flexible shaft, not shown in FIG. 3, a flexible image conductor 56 is situated into which the signal radiation from the observed area is coupled by a symbolically indicated endoscope objective lens 57. Images of the observed area are generated onto the sensor surfaces of the image sensor 53 as well as of the image sensor 55 by an imaging lens that is situated in the proximal end portion 54 of the endoscope 50 and not illustrated, as well as, in some cases, an adaptive lens. Situated in the distal end portion 51 of the endoscope 50 are two coils 58, 58' of a position-recording system, whose windings surround the image conductor 58 in a compact arrangement. As explained with reference to FIG. 2, with the data supplied by the position-recording system, it is possible to determine a correspondence between lighting elements and scene regions of a captured image.

With additional, non-illustrated embodiments of the inventive apparatus, which otherwise are configured as is shown in FIG. 2 or FIG. 3, the image sensor can be connected via a flexible image conductor with the proximal end of the shaft. Consequently, operation of the endoscope is substantially facilitated.

Figure 4:
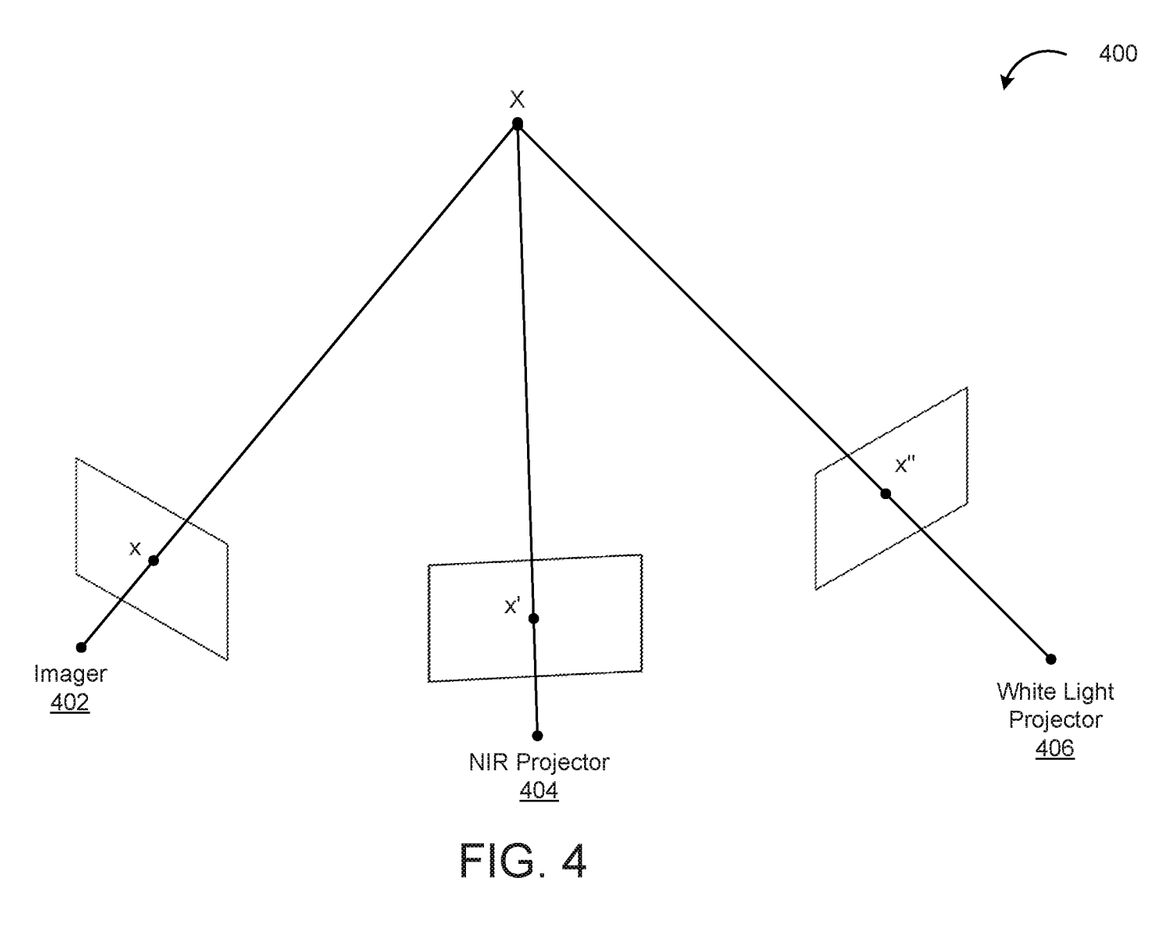
FIG. 4 is an example process flow diagram for determining automated actions in accordance with one or more embodiments of the disclosure.

FIG. 4 illustrates a diagram 400 of a trifocal tensor relationship between a scene point X and an imager 402, near-infrared (NIR) projector 404, and white light projector 406.

A scene may refer to a scene of a hollow organ or cavity in a body with varied topography, depth, etc. and scene point X may refer to an individual point within the scene. Scenes may be captured and rendered as 2D images and may be illuminated by various projectors. For example, rays of scene point X may pass through a first imaging plane of imager 402 (e.g., camerahead) with a first center of projection C and correspond to a first pixel x at imager 402. In this way, an image of a scene can be constructed by imager 402. Likewise, a scene can be illuminated by projectors. NIR projector 404 may project a NIR constellation onto the scene. A NIR constellation point projected through x' may correspond to scene point X, and a visible light projector with pixel x" turned on to hit the same scene point X.

NIR projector 404 may be used to project a predetermined pattern onto a scene, such as a pattern of concentric circles, horizontal and/or vertical bars, and so forth. The projected pattern may be captured at imager 402 and then processed to identify any deformations based on the geometry of the scene that the pattern was projected on. Based on these deformations, a light-to-region correspondence may be computed, rather than tentatively assumed. The correspondences described above may be used to perform adaptive lighting techniques. The pixel intensity measured at x by imager 402 may be used to determine the drive strength of white light projector 406 at x". Alternatively, the rendering of pixel x could adjust for (e.g., normalize) the known drive strength at x".

In some embodiments, a beam splitter is used to establish a correspondence between illumination rays of a projector and imaging rays of a camera by establishing a common center of projection between the projector(s) and imager(s). A correspondence can be established at manufacturing time via calibration so that it does not vary significantly with scene geometry, in such embodiments, stereo triangulation may be avoided.

According to an aspect of at least one embodiment, an endoscope includes multiple lighting elements with independent drive strengths. Examples of lighting elements include light fibers, discrete LEDs, digital micromirror devices, and so forth. The multiple lighting elements may be configured to illuminate overlapping or potentially overlapping regions. Dependent control in this context may refer to the drive strengths of a first lighting element and a second lighting element being considered in conjunction with each other. For example, if the first lighting element and the second lighting element overlap a region, then the drive strength of the first lighting element and second lighting elements may be computed so that they the combined intensity of the first and second drive strength is at a desired level. The drive strengths of the multiple lighting elements may be dependently controlled to light a scene.

According to an aspect of at least one embodiment, a method is described herein to dynamically determine which lighting elements illuminate which portions of a region. The determination may be performed programmatically and in real-time or near real-time. This may differ from conventional techniques where the correspondence of lighting elements to regions may be fixed and/or assumed to be fixed. Such assumptions may be unrealistic and/or impractical for use in endoscopes, as the geometry of scenes that are being captured during endoscope procedures may differ, such that assumptions of planar geometries and/or correspondences may result in poor or sub-par lighting.

According to an aspect of at least one embodiment, a method is described herein to determine in real-time or near real-time the light intensity of multiple regions within a scene, possibly using a bilateral filter.

According to an aspect of at least one embodiment, a method is described herein to derive the appropriate drive level for each lighting element based on the measured intensity of each scene region. In various embodiments, the control of multiple independent light sources acting on somewhat independent scene regions may be coordinated programmatically in real-time or near real-time. For example, there may be certain scene regions in which multiple light elements contribute illumination, and the signal may be split appropriately between the light elements. The drive strength provided to regions of higher reflectivity (e.g., where a metallic instrument is located) may be reduced, the drive strength to other regions such as body cavities may be increased to provide greater visibility to an interior body cavity, etc.

According to an aspect of at least one embodiment, a method is described herein to perform motion tracking and prediction to identify different objects in a frame and adjust illumination levels based on properties of the object. For example, frames of a video may be extracted to identify an object, such as a metallic tool. The metallic tool may be highly reflective, and lighting elements that contribute to the region of the scene in which the metallic tool is located may be adjusted to reduce the overall intensity of light delivered to that region. Once the object has been identified as being highly reflective, the object may be tracked through the scene as it moves, and a reduced light intensity may be delivered to the region of the scene that the object occupies as it moves. In some cases, a reduced intensity level is determined for a metallic tool, and that reduced intensity level is maintained for the region of the frame that is occupied by the tool as it moves through the scene.

Figure 5:
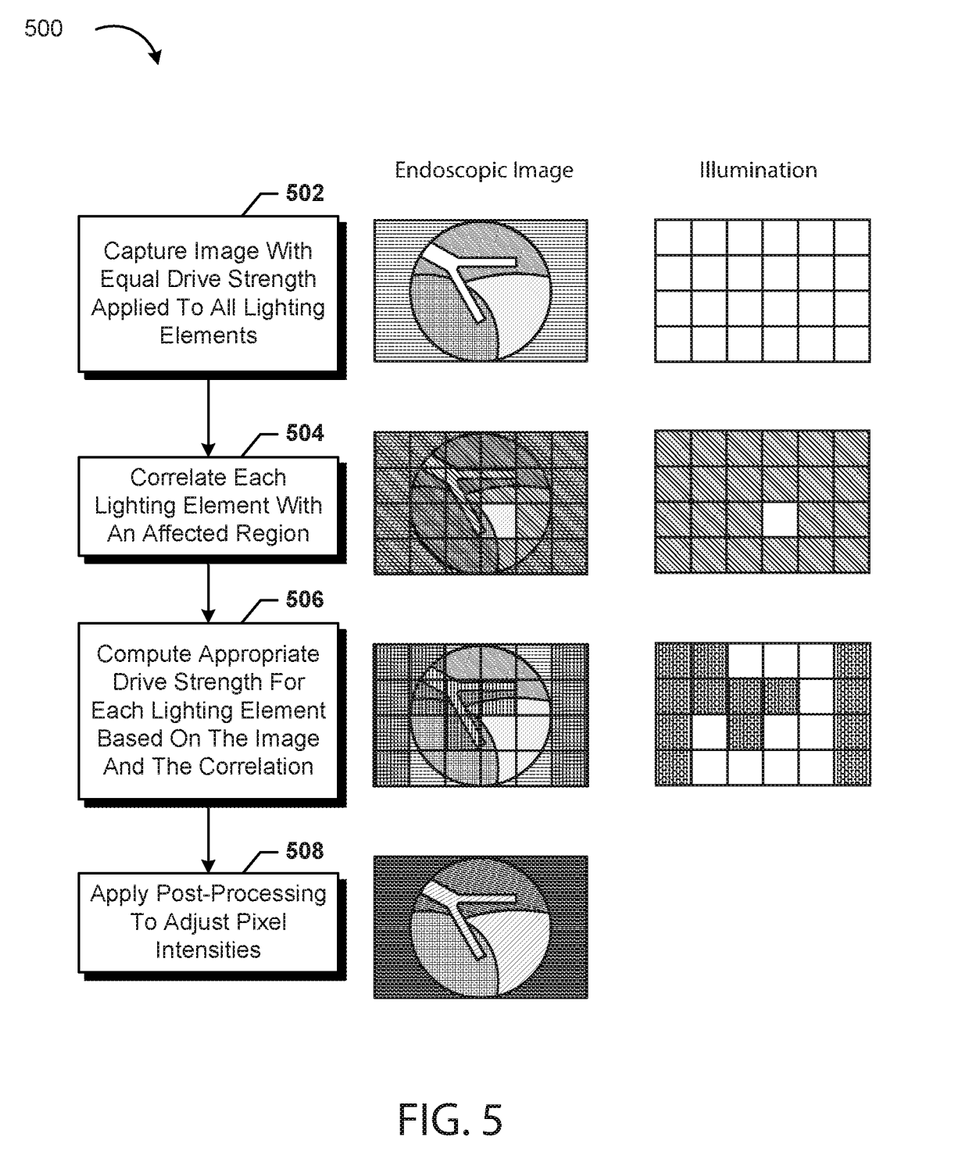
FIG. 5 depicts an example hybrid process and data flow in accordance with one or more embodiments of the disclosure.

FIG. 5 depicts a process 500 for endoscope adaptive light, according to at least one embodiment, that may be performed using a number of lighting elements whose illumination regions may overlap and change, based on the topography of the scene. The correspondences for each lighting element to the scene may be non-fixed in such a manner that it is disadvantageous or impractical to assume a correspondence. The lighting system may be initialized in a first step 502 to capture a standard image where equal drive strengths are applied to all light elements. This may be used to identify regions that are over-exposed and/or under-exposed. For example, metallic instruments may be over-exposed.

In a second step 504, each lighting element may be correlated with affected scene region. This may be performed in various ways. For example, one lighting element may be turned on at a time to isolate the effects of each lighting element on a scene. This may be performed as part of a calibration process. Correspondences of the lighting elements to their affected scene regions may be computed continuously, on a scheme, and so forth. In some embodiments, correspondences for lighting elements are computed in a round-robin fashion. For example, a first lighting element may be perturbed (e.g., intensity is increased or decreased), the effect of the perturbation on the scene may be captured to determine a first correspondence, and then the first lighting element may be un-perturbed (e.g., reversing an increase or decrease in drive strength). Then, a second lighting element may be perturbed to determine a second correspondence, and then un-perturbed once the second correspondence is determined, and so forth. In some embodiments, perturbation is calibrated based on the frame capture rate of a camerahead. For example, if the camerahead captures video frames at 60 frames-per-second (60 fps), then lighting elements may be perturbed one at a time for $\frac{1}{60}^{th}$ of a second in succession. For example, if there are 6 lighting elements, then the correspondences for all 6 lighting elements may be established in $\frac{1}{10}^{th}$ of a second.

In various embodiments, structured light may be used to determine the correspondences of a lighting element to its illumination regions. Structured light is the process of projecting a known pattern (e.g., grids or horizontal bars) on to a scene. The way that these deform when striking surfaces allows vision systems to calculate the depth and surface information of the objects in the scene, as used in structured light 3D scanners. Determining how the projected patterns are deformed may be used to establish a correspondence between a lighting element and a scene region. In various embodiments, a constellation pattern may be spatially encoded into an illumination using near-infrared (NIR) wavelengths ranging from 0.7 to 1.4 microns. The use of NIR or other non-visible light does not interfere with visible imaging. In some cases, visible light may be used to temporarily project structured light frames through the use of a frame buffer.

In various embodiments, once the correspondences of each light element are computed, a third step 506 includes computing an appropriate drive strength for each lighting element to determine how to better expose each region. For example, a region that is over-exposed may be corrected by reducing the drive strength of any suitable combination of lighting elements that correspond to that region. It should be noted that different scene regions may require different levels of illumination, and that this illumination may be provided by any of an array of multiple lighting elements that affect the respective regions. For example, consider an illustrative scene with 9 scene regions that are organized as a 3×3 square matrix. The intensities of each scene region may be measured as $I_{1,1}$ thru $I_{3,3}$:

| $I_{1,1}$ | $I_{1,2}$ | $I_{1,3}$ |
| $I_{2,1}$ | $I_{2,2}$ | $I_{2,3}$ |
| $I_{3,1}$ | $I_{3,2}$ | $I_{3,3}$ |

Assume also that there are, for example, n lighting elements. Each lighting element may be correlated to each scene region to determine weights for how each region is affected by the drive strength of the lighting elements. The overall contribution $W_{x,y}$ of each lighting element $w^{1 \cdots n}$ to each region may be defined as:

$$W_{x,y} = w_{x,y}^1 + w_{x,y}^2 + \ldots + w_{x,y}^n$$

Overall contributions to each region may be normalized so that $w_{x,y}^i$ represents a proportion or percentage contribution of intensity to region x, y by the i-th lighting element. The contribution weights for the 3×3 square matrix may be defined as:

| $W_{1,1}$ | $W_{1,2}$ | $W_{1,3}$ |
| $W_{2,1}$ | $W_{2,2}$ | $W_{2,3}$ |
| $W_{3,1}$ | $W_{3,2}$ | $W_{3,3}$ |

A target intensity level T may be determined for each region. The target intensity level may be the same value across each scene region. For example, an operator may select a higher or lower intensity level for the entire scene via a graphical user interface to increase or decrease the illumination for the entire scene. In some embodiments, the same target intensity level T is set for each region, and a system of equations may be solved to determine appropriate adjusted weights $W_{x,y}'$ for each scene region, wherein the drive strengths of the individual lighting elements are variables that are to be solved to determine how the target intensity level T may be achieved for each region. In some embodiments, a tolerance for each region may be provided so that if the weights result in an intensity value that is within a tolerance $\Delta T$, that it is still an acceptable drive strength. In some embodiments, the system of equations selected based on regions that are over-exposed and/or underexposed. This may be used as a technique to improve the computational performance of the system, as well as to quickly resolve and fix the illumination being provided to the regions that are most difficult for a viewer to see clearly. This may be useful in various cases, such as where there are a limited number of lighting elements that can be adjusted to achieve the desired lighting.

In some embodiments, a fourth step 508 includes performing post-processing to adjust pixel intensities to compensate for local illumination level. These techniques may utilize HDR fusion techniques such as exposure-bracketing and tone-mapping. Relative to the standard image, there may be improved visibility of dark background anatomy, and reduced visibility of unwanted flare.

Techniques described herein may be utilized in combination with each other, according to at least one embodiment. For example, drive strengths for a number of lighting elements may be used to reduce the extreme illumination regions that are over-exposed to be within the dynamic range of a typical imager, and then the captured images may be post-processed using HDR techniques. This has various advantages over techniques that perform HDR without adaptive lighting. Typically, HDR algorithms that combine images at different exposures require some amount of overlap in the instantaneous dynamic range of each image. Because the light intensity associated with a highlight or metallic tool may be many orders of magnitude brighter than surrounding tissue, it may be necessary to acquire an unreasonable number of images spanning these extremes with sufficient overlap in adjacent exposures. Such onerous and/or unrealistic requirements may be obviated through the use of adaptive lighting techniques.

In some embodiments, correlating light elements to scene regions may be done as a manufacturing calibration step if the correspondence between rays of illumination light and image formation rays reflected by the scene is fixed. It should be noted, however, that a fixed correspondence is not required, and in some embodiments, it may even be expected that the correspondences are dynamic and may change in dynamic scenes. The optically aligned projector/beam splitter/sensor scheme described by Charette et al is an example such as a system. If these rays are not guaranteed to be coincident, the correspondence to pixels will vary with scene geometry. In this case the correspondence step can be done actively at runtime using stereo triangulation as is done with structured light camera, or in a "brute force" manner in which each light element is examined individually. An improved correspondence determination technique could include the use of linear combinations of light elements to solve for the contribution of each element. An example of this approach would be to active odd-only elements, then even-only, then left-half-only, then right-half-only. Solving a system of equations could derive the contribution of each element without needing to restrict imaging to one light element at a time.

In some embodiments, motion tracking and/or object tracking techniques may be used in connection with various techniques described herein. For example, image processing techniques may be used to extract a set of features from a captured image. A feature may refer to some discrete portion of a capture image that may be of interest. For example, a metallic tool within a body cavity may be identified as a feature. The portion of an image that is occupied by a feature may be referred to as a patch. Continuing with the previous example, each patch may be analyzed to determine whether to track the feature. For example, the illumination intensity of each feature may be computed as an average of the intensity values of each pixel that the patch occupies. Features that are considered over-exposed or under-exposed may be tracked. Each tracked object may have a specific target intensity value that is selected to reduce or increase the overall illumination provided to the scene region that is occupied by the object. For example, a goal of such a system may be to identify certain highly-reflect objects—such as metallic tools—and then track those objects and provide a reduced level of illumination to those scene regions, to reduce the visibility of unwanted flare.

Invisible (or imperceptible) structured light uses structured light without interfering with other computer vision tasks for which the projected pattern will be confusing. Example methods include the use of infrared light or of extremely high frame rates alternating between two exact opposite patterns.

Figure 6:
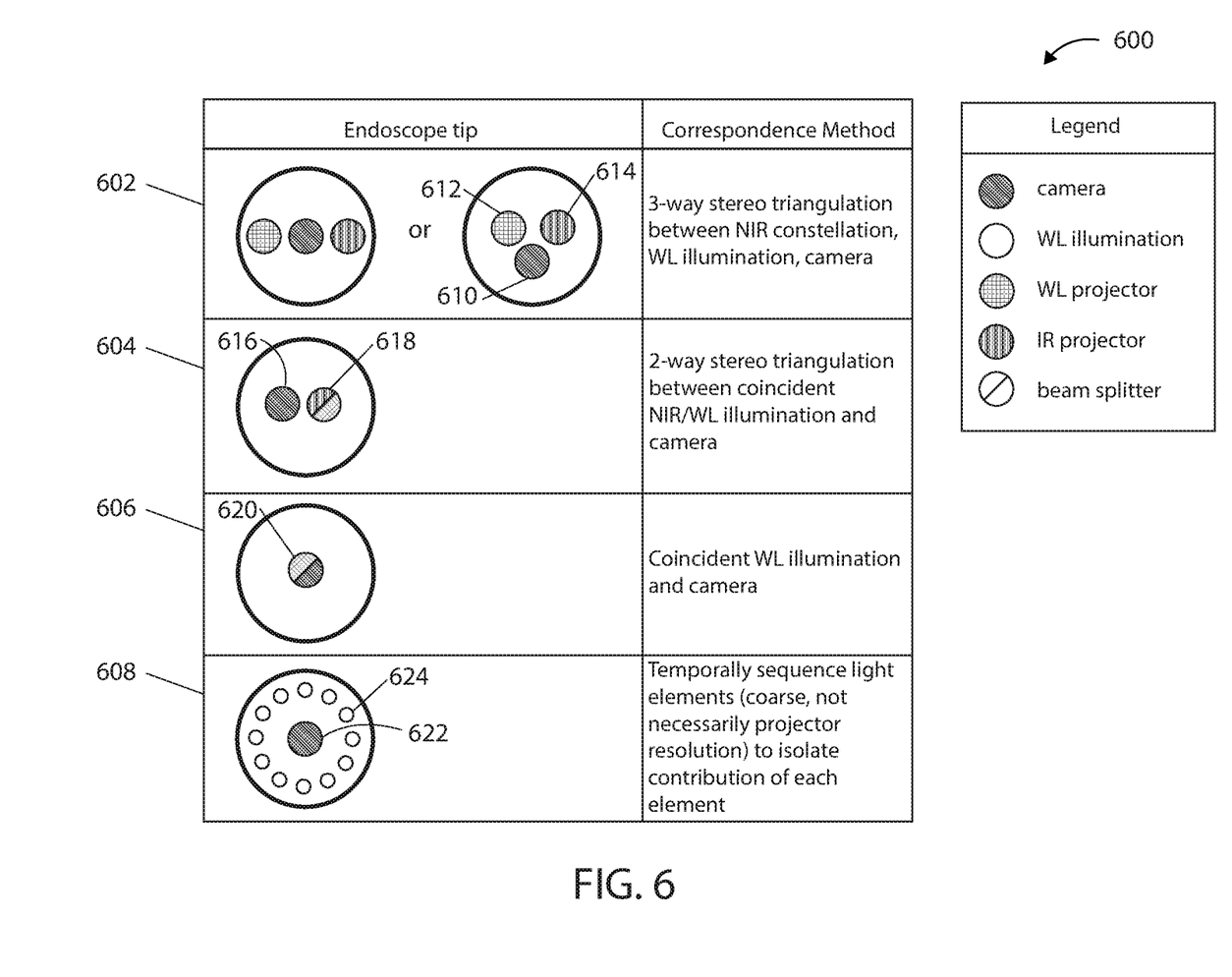
FIG. 6 is an example use case for automated endoscopic device control systems in accordance with one or more embodiments of the disclosure.

FIG. 6 illustrates example endoscope tips, according to various embodiments. Other components may be incorporated into the endoscope tips depicted in FIG. 6. For example, other elements, such as a camerahead or imaging sensor may be used to capture video and/or still images from the distal end.

In at least one embodiment, a first endoscope tip 602 depicted in FIG. 6 depicts three discrete components—a camera 610, a first lighting element 612 (e.g. first projector) that provides white light (WL) illumination, and a second lighting element 614 (e.g. second projector) that provides infrared (IR) illumination. IR illumination may be used to project a constellation pattern using a wavelength that is not visible to the naked eye, so as to not distract or alter a user's perceptions. WL illumination may be used to provide white light or other visible light to illumination a scene or scene region, so as to provide the human user with images that s/he can use to perform an endoscopic procedure. A camera or other imaging sensor may be used to capture video and/or still images, for example, from an interior body cavity.

In at least one embodiment, a second endoscope tip 604 depicted in FIG. 6 depicts two discrete components—a camera 616, and a lighting element 618 (e.g. projector). The lighting element may be a project that provides both NIR and WL illumination. A beam splitter may be used to split illumination provided by a projector into a number of portions including an imaging portion and reactive control portions—for example, to provide for WL illumination and IR illumination simultaneously.

In at least one embodiment, a third endoscope tip 606 depicted in FIG. 6 depicts one discrete component 620. The discrete component may include coincident WL illumination and camera in an integrated unit. In some embodiments, WL illumination is used to determine the correspondence between the lighting element and one or more scene regions.

In at least one embodiment, a fourth endoscope tip 608 depicted in FIG. 6 depicts a camera 622 and a number of lighting elements (e.g., lighting element 624). Temporal sequencing may be used to isolate the contribution of each lighting element to different portions of a scene. The lighting elements depicted herein may be coarse, not necessarily projector resolution.

In the state of the art, it is known to guide the light guide elements between an outer shaft and an inner shaft of the endoscope to the distal end, the outer surface of the outer shaft realizing the outer limit of the endoscope and the inner shaft being provided for the reception of imaging optics.

Figure 7:
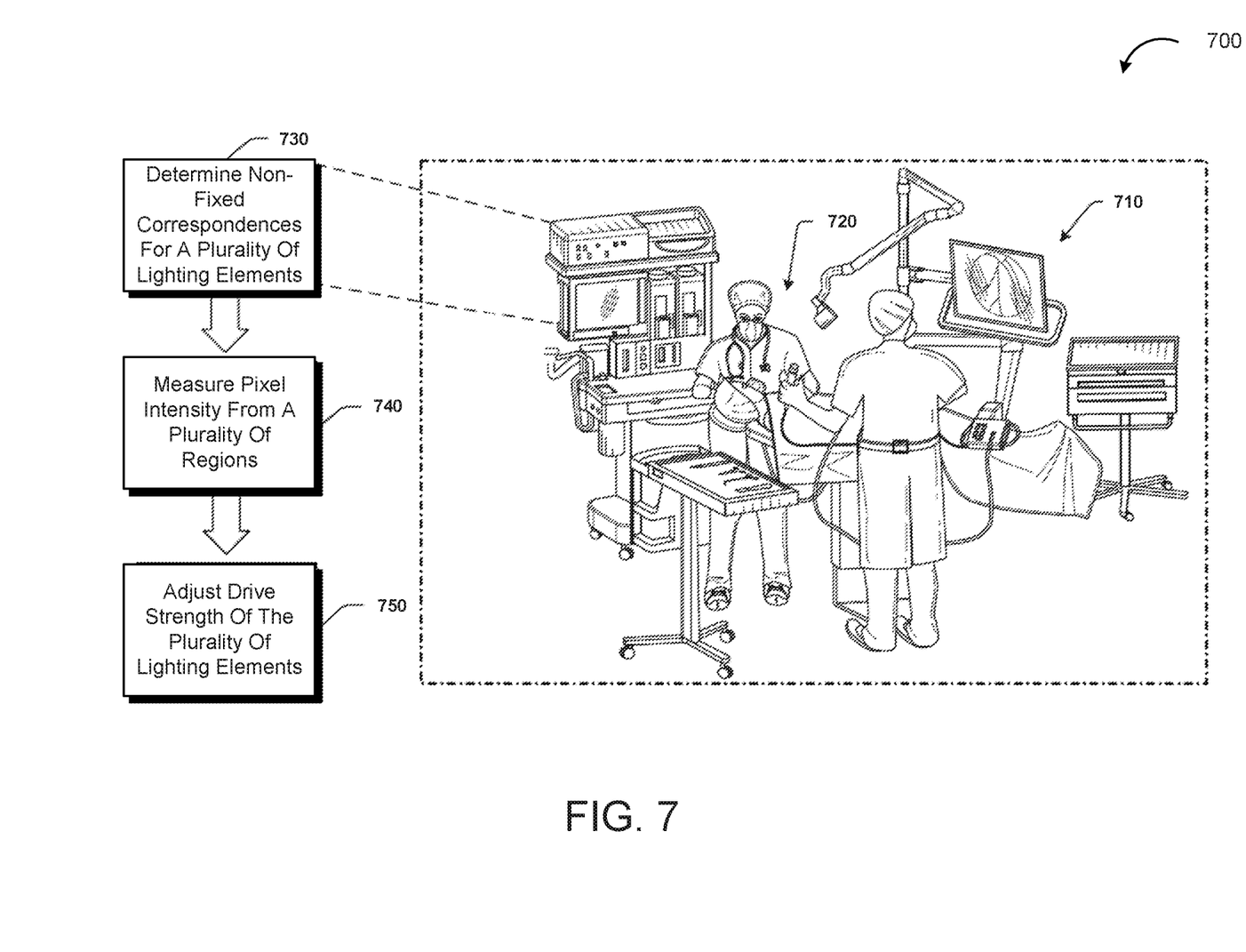
FIG. 7 schematically illustrates an example architecture of a neural network server in accordance with one or more embodiments of the disclosure.

FIG. 7 depicts an example use case 700 for automated endoscopic device control systems in accordance with one or more embodiments of the disclosure. In FIG. 7, an endoscopic system of devices 710 may include a camera system 720. The camera system may include a distal end, wherein the distal end includes a number of lighting elements and a camera or camerahead for capturing images from the distal end. The distal end of the camera system 720 may be used to capture images of an interior body cavity in which a surgical manipulation is to be performed.

In at least one embodiment, the camera system 720 is configured to programmatically perform adaptive lighting techniques. In at least one embodiment, a first step 730 includes determining correspondences for a number of lighting elements onto a scene or scene region. The correspondences may be determined using structured light, or other techniques to measure correspondences using non-visible light. In some cases, correspondences may be determined using visible light, for example, by perturbing the illumination of a scene for a short duration—perhaps for the length of a single frame that can be captured by an imaging sensor. A scene captured by an imaging sensor may be divided into a number of regions (e.g., in a square or rectangular grid), and the contribution of each lighting element onto each scene region may be computed. In at least one embodiment, a second step 740 includes measuring the light intensity delivered to each region, and a third step 750 includes determining how to adjust the drive strength of the number of lighting elements. A system of equations may be solved or otherwise optimized to improve the lighting of the scene. For example, white light illumination to scene regions that over-exposed may be reduced, whereas illumination to scene regions that are under-exposed may be increased.

One or more operations of the method, process flows, or use cases of FIGS. 1-7 may have been described above as being performed by a user device, or more specifically, by one or more program module(s), applications, or the like executing on a device using hardware and/or software. It should be appreciated, however, that any of the operations of methods, process flows, or use cases of FIGS. 1-7 may be performed, at least in part, in a distributed manner by one or more other devices, or more specifically, by one or more program module(s), applications, or the like executing on such devices. In addition, it should be appreciated that processing performed in response to execution of computer-executable instructions provided as part of an application, program module, or the like may be interchangeably described herein as being performed by the application or the program module itself or by a device on which the application, program module, or the like is executing. While the operations of the methods, process flows, or use cases of FIGS. 1-7 may be described in the context of the illustrative devices, it should be appreciated that such operations may be implemented in connection with numerous other device configurations.

The operations described and depicted in the illustrative methods, process flows, and use cases of FIGS. 1-7 may be carried out or performed in any suitable order, such as the depicted orders, as desired in various example embodiments of the disclosure. Additionally, in certain example embodiments, at least a portion of the operations may be carried out in parallel. Furthermore, in certain example embodiments, less, more, or different operations than those depicted in FIGS. 1-7 may be performed.

Although specific embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and flow diagrams, and combinations of blocks in the block diagrams and the flow diagrams, respectively, may be implemented by execution of computer-executable program instructions. Likewise, some blocks of the block diagrams and flow diagrams may not necessarily need to be performed in the order presented, or may not necessarily need to be performed at all, according to some embodiments. Further, additional components and/or operations beyond those depicted in blocks of the block and/or flow diagrams may be present in certain embodiments.

Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, may be implemented by special-purpose, hardware-based computer systems that perform the specified functions, elements or steps, or combinations of special-purpose hardware and computer instructions.

What is claimed is:

1. An endoscope system for capturing a scene, comprising:
  a plurality of lighting elements located at a distal end;
  a camerahead for capturing a first set of one or more images of the scene;
  a beam splitter that establishes a fixed correspondence between illumination rays of the first lighting element and imaging rays of the camerahead, both imaging rays and illumination rays from at least a first lighting element of the plurality of lighting elements passing therethrough; and
  software and/or hardware comprising at least one process, wherein the at least one process is configured to:
  determine correspondences between a plurality of regions of the first set of one or more images and the first lighting element of the plurality of lighting elements;
  determine pixel intensities at the plurality of regions;
  determine a first drive strength for the first lighting element based on the correspondences and the pixel intensities; and
  cause the first drive strength to be applied by the first lighting element.

2. The endoscope system of claim 1, wherein the at least one process is configured to:
  obtain, from the camerahead, a second set of one or more images of the scene that are illuminated by the plurality of lighting elements after the first drive strength was applied by the first lighting element; and
  perform one or more digital image post-processing techniques on the second set of one or more images.

3. The endoscope system of claim 2, wherein the one or more digital image post-processing techniques comprises at least one of: exposure-bracketing and tone-mapping.

4. The endoscope system of claim 1, wherein at least one of the plurality of lighting elements emits light in one or more non-visible wavelengths.

5. The endoscope system of claim 4, wherein the one or more non-visible wavelengths range from 0.7 to 1.4 microns.

6. The endoscope system of claim 1, wherein the at least one process is configured to determine drive strengths for the plurality of lighting elements by at least solving a system of equations based at least in part on target pixel intensities for the plurality of regions.

7. The endoscope system of claim 1, wherein the at least one process is configured to determine the correspondences for the plurality of regions of the scene by at least:
determine, from the first set of one or more images, at least one feature;
determine the feature is over-exposed in the first set of one or more images;
determine a target pixel intensity for the feature;
track the feature through a second set of one or more images; and
illuminate the feature in the second set of one or more images according to the target pixel intensity.

8. The endoscope system of claim 1, wherein a first illumination region of a first lighting element at least partially overlaps with a second illumination region of a second lighting element.

9. The endoscope system of claim 1, wherein:
a first region of the plurality of regions is under-exposed in the first set of one or more images; and
as a result of the first drive strength being applied by the first lighting element, illumination to the scene region corresponding to the first region is increased.

10. A method for providing adaptive lighting to a scene, comprising:
capturing, by a camerahead, a first set of one or more images of the scene that is illuminated by a plurality of lighting elements; and
determining correspondences between a plurality of regions of the scene based on the first set of one or more images and a first lighting element of the plurality of lighting elements;
determining pixel intensities at the plurality of regions;
identifying at least one feature present in the first set of one or more images;
determining that the feature is over-exposed or under-exposed;
determining a target pixel intensity for the feature;
determining a first drive strength for the first lighting element based on the correspondences and the pixel intensities and the target pixel intensity for the feature;
tracking a motion of the feature through a second set of one or more images; and
illuminating the feature in the second set of one or more images according to the target pixel intensity.

11. The method of claim 10, further comprising the steps of:
capturing, from the camerahead, the second set of one or more images of the scene that are illuminated by the plurality of lighting elements after the first drive strength was applied by the first lighting element; and
performing one or more digital image post-processing techniques on the second set of one or more images.

12. The method of claim 11, wherein the one or more digital image post-processing techniques comprises at least one of: exposure-bracketing and tone-mapping.

13. The method of claim 10, wherein the step of determining the correspondences for the plurality of regions of the scene further comprises the steps of:
identifying a predetermined pattern;
determining, from a first image of the first set of one or more images, an actual pattern projected onto the scene by the first lighting element using one or more non-visible wavelengths; and
determining second correspondences for the first lighting element based on a comparison of the predetermined pattern and the actual pattern.

14. The method of claim 13, wherein the one or more non-visible wavelengths range from 0.7 to 1.4 microns.

15. The method of claim 10, wherein the step of determining the drive strengths for the plurality of lighting elements comprises solving a system of equations based at least in part on target intensities for the plurality of regions.

16. The method of claim 10, wherein the tracking the motion of the feature includes the step of predicting the motion of the feature in the second set of one or more images.

17. The method of claim 10, wherein a first illumination region of the first lighting element at least partially overlaps with a second illumination region of a second lighting element.

18. The method of claim 10, wherein a beam splitter is used to establish a fixed correspondence between illumination rays of the first lighting element and imaging rays of the camerahead.

19. The method of claim 10, wherein:
a first region of the plurality of regions is under-exposed in the first set of one or more images; and
as a result of the first drive strength being applied by the first lighting element, illumination to a scene region corresponding to the first region is increased.

* * * * *